United States Patent
Hohlweg

(10) Patent No.: US 8,378,097 B2
(45) Date of Patent: Feb. 19, 2013

(54) 3-(1,3-BENZODIOXOL-5-YL)-6-(4-CYCLO-PROPYLPIPERAZIN-1-YL)-PYRIDAZINE, ITS SALTS AND SOLVATES AND ITS USE AS HISTAMINE H3 RECEPTOR ANTAGONIST

(75) Inventor: Rolf Hohlweg, Humblebaek (DK)

(73) Assignee: High Point Pharmaceuticals, LLC, High Point, NC (US)

( * ) Notice: Subject to any disclaimer, the term of this patent is extended or adjusted under 35 U.S.C. 154(b) by 504 days.

(21) Appl. No.: 12/302,132

(22) PCT Filed: May 22, 2007

(86) PCT No.: PCT/EP2007/054940
§ 371 (c)(1),
(2), (4) Date: Nov. 24, 2008

(87) PCT Pub. No.: WO2007/137968
PCT Pub. Date: Dec. 6, 2007

(65) Prior Publication Data
US 2009/0176793 A1    Jul. 9, 2009

(30) Foreign Application Priority Data

May 29, 2006  (EP) .................... 06114615
Sep. 5, 2006   (EP) .................... 06120117

(51) Int. Cl.
C07D 237/02   (2006.01)
A61K 31/50    (2006.01)
(52) U.S. Cl. ......... 544/224; 514/183; 514/247; 514/449
(58) Field of Classification Search ................. 514/183, 514/247, 449; 544/224
See application file for complete search history.

(56) References Cited

U.S. PATENT DOCUMENTS

| | | | |
|---|---|---|---|
| 2,993,899 A | 7/1961 | Dawson |
| 3,309,370 A | 3/1967 | Schut |
| 3,753,988 A | 8/1973 | Rodway et al. |
| 3,886,161 A | 5/1975 | Hardtmann |
| 4,026,891 A | 5/1977 | Austel et al. |
| 4,163,849 A | 8/1979 | Lumma, Jr. et al. |
| 4,223,036 A | 9/1980 | Heeres et al. |
| 4,251,658 A | 2/1981 | Szilagyi et al. |
| 4,265,894 A | 5/1981 | Gootjes |
| 4,339,579 A | 7/1982 | Freed |
| 4,616,014 A | 10/1986 | Teraji et al. |
| 4,673,675 A | 6/1987 | Robba et al. |
| 4,758,566 A | 7/1988 | Uno et al. |
| 4,824,846 A | 4/1989 | Kampe et al. |
| 4,935,426 A | 6/1990 | Zipplies et al. |
| 5,001,125 A | 3/1991 | Stokbroekx et al. |
| 5,670,505 A | 9/1997 | Matsuo et al. |
| 5,929,089 A | 7/1999 | Jegham et al. |
| 6,130,217 A | 10/2000 | Arnold et al. |
| 6,316,475 B1 | 11/2001 | Bennani et al. |
| 6,864,261 B2 | 3/2005 | Gharagozloo et al. |
| 6,906,060 B2 | 6/2005 | Peschke et al. |
| 7,115,634 B2 | 10/2006 | Thurieau et al. |
| 7,186,721 B2 | 3/2007 | Peschke et al. |
| 7,229,997 B2 | 6/2007 | Nilsson et al. |
| 7,294,626 B2 | 11/2007 | Hohlweg |
| 7,494,994 B2 | 2/2009 | Desos et al. |
| 7,494,995 B2 | 2/2009 | Desos et al. |
| 7,547,693 B2 | 6/2009 | Ohtake et al. |
| 2003/0073672 A1 | 4/2003 | Breitenbucher et al. |
| 2003/0236259 A1* | 12/2003 | Hohlweg et al. .............. 514/242 |
| 2004/0023946 A1 | 2/2004 | Peschke et al. |
| 2006/0293310 A1 | 12/2006 | Abouabdellah et al. |
| 2009/0176793 A1 | 7/2009 | Hohlweg |
| 2009/0264435 A1 | 10/2009 | Hohlweg et al. |
| 2009/0312309 A1 | 12/2009 | Hohlweg et al. |
| 2010/0267721 A1 | 10/2010 | Hohlweg et al. |
| 2010/0298316 A1 | 11/2010 | Dorwald et al. |
| 2011/0071159 A1 | 3/2011 | Lundbeck et al. |

FOREIGN PATENT DOCUMENTS

| | | |
|---|---|---|
| AU | 639539 | 7/1993 |
| DE | 2609746 A1 | 10/1976 |
| DE | 2804096 A1 | 8/1978 |
| DE | 2824764 A1 | 12/1979 |
| DE | 3803860 A1 | 8/1989 |
| EP | 0034752 B1 | 6/1983 |
| EP | 0236140 A2 | 9/1987 |
| EP | 0459819 A2 | 12/1991 |
| EP | 0327912 B1 | 4/1992 |

(Continued)

OTHER PUBLICATIONS

Grant & Grant, Chemical Dictionary, 5th Edition, p. 147 and 289.*

(Continued)

*Primary Examiner* — Sreeni Padmanabhan
*Assistant Examiner* — Shobha Kantamneni
(74) *Attorney, Agent, or Firm* — Samuel B. Rollins

(57) ABSTRACT

3-(1,3-Benzodioxol-5-yl)-6-(4-cyclopropylpiperazin-1-yl) pyridazine and salts and solvates thereof, having histamine H3 antagonistic activity can be used in pharmaceutical compositions.

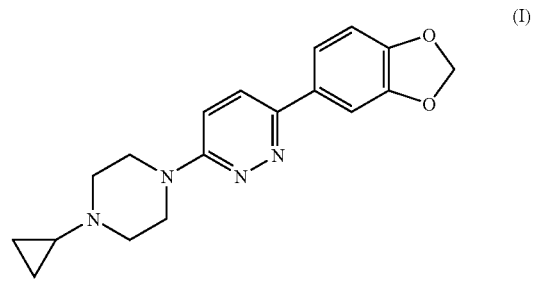

(I)

11 Claims, No Drawings

FOREIGN PATENT DOCUMENTS

| | | |
|---|---|---|
| EP | 0385237 B1 | 6/1994 |
| EP | 0320032 B1 | 1/1995 |
| EP | 0978512 A1 | 2/2000 |
| EP | 1721896 A1 | 11/2006 |
| EP | 1721897 A1 | 11/2006 |
| EP | 1020445 B1 | 8/2008 |
| GB | 753166 | 7/1956 |
| GB | 1345880 | 2/1974 |
| WO | WO 94/14780 A1 | 7/1994 |
| WO | WO 94/22846 A | 10/1994 |
| WO | WO 97/02245 A1 | 1/1997 |
| WO | WO 97/17345 A1 | 5/1997 |
| WO | WO 98/27081 A1 | 6/1998 |
| WO | WO 99/21845 A2 | 5/1999 |
| WO | WO 99/42458 A1 | 8/1999 |
| WO | WO 00/66578 A1 | 11/2000 |
| WO | WO 01/32646 A2 | 5/2001 |
| WO | WO 01/32659 A1 | 5/2001 |
| WO | WO 01/42241 A1 | 6/2001 |
| WO | WO 01/44201 A | 6/2001 |
| WO | WO 01/64645 A2 | 9/2001 |
| WO | WO 01/66534 A2 | 9/2001 |
| WO | WO 01/74773 A2 | 10/2001 |
| WO | WO 01/74810 A2 | 10/2001 |
| WO | WO 01/74813 A2 | 10/2001 |
| WO | WO 01/74814 A1 | 10/2001 |
| WO | WO 01/74815 A2 | 10/2001 |
| WO | WO 02/12190 A | 2/2002 |
| WO | WO 02/060392 A2 | 8/2002 |
| WO | WO 03/066604 A2 | 6/2003 |
| WO | WO 03/104235 A1 | 12/2003 |
| WO | WO 2004/054973 A2 | 7/2004 |
| WO | WO 2005/009976 A1 | 2/2005 |
| WO | WO 2005/100344 A1 | 10/2005 |
| WO | WO 2006/004589 A2 | 1/2006 |
| WO | WO 2006/050389 A2 | 5/2006 |
| WO | WO 2006/058649 A1 | 6/2006 |
| WO | WO 2006/077387 A2 | 7/2006 |
| WO | WO 2006/113704 A2 | 10/2006 |
| WO | WO 2007/003604 A2 | 1/2007 |
| WO | WO 2007/011820 A2 | 1/2007 |
| WO | WO 2007/016496 A2 | 2/2007 |

OTHER PUBLICATIONS

Vippagunta et al. (see Advanced Drug Delivery Reviews 48, 2001, pp. 3-26.*

Greene et al., Protecting Groups in Organic Synthesis, Third Edition, 1999, pp. 287, 720.*

Pending claims for U.S. Appl. No. 11/917,823, filed Jun. 8, 2009.

Pending claims for U.S. Appl. No. 12/294,756, filed Sep. 26, 2008.

Pending claims for U.S. Appl. No. 12/301,919, filed Nov. 21, 2008.

Pending claims for U.S. Appl. No. 12/367,952, filed Feb. 9, 2009.

Pending claims for U.S. Appl. No. 12/663,103, filed Jun. 25, 2010.

Hanson et al., "Phenylpiperazine-Based Radiopharmaceuticals for Brain Imaging. 3. Synthesis and Evaluation of Radioiodinated 1-Alkyl-4-phenylpiperazines," Journal of Medicinal Chemistry, 30(1):29-34 (1987).

Lovenberg et al., "Cloning and Functional Expression of the Human Histamine H3 Receptor," Molecular Pharmacology, 55:1101-1107 (1999).

Green et al., "The Role of Protective Groups in Organic Synthesis", Protective Groups in Organic Synthesis, Third Edition, John Wiley & Sons, Inc., pp. 1, 270 and 720.

Abdel-Magid et al., "Reductive Amination of Aldehydes and Ketones with Sodium Triacetoxyborohydride. Studies on Direct and Indirect Reductive Amination Procedures," J. Org. Chem., 61(11):3849-3862 (1996).

Adam et al., "Concise Synthesis of 1H-Pyrazin-2-ones and 2-Aminopyrazines," Synlett, No. 11:2031-2033 (2004).

Ballaben et al., "Reactivity of cyclopentanone enamines towards non-symmetric electrophilic diazenes," Gazzetta Chimica Italiana, 123(7):387-391 (1993) (abstract only).

Brown et al., "Unfused Heterobicycles as Amplifiers of Phleomycin. III. Thiazolylpyridines and Bipyrimidines with Strongly Basic Side Chains," Australian Journal of Chemistry, 34:2423-2429 (1981).

Byrn et al., "Hydrates and Solvates," Solid-State Chemistry of Drugs, 2d, Chapter 11, 233-247 (1999).

Celanire et al., "Keynote review: Histamine H3 receptor antagonists reach out for the clinic," Drug Discovery Today, 10(23/24):1613-1627 (2005).

Contreras et al., "Aminopyridazines as Acetylcholinesterase Inhibitors," J. Med. Chem., 42:730-741 (1999).

Contreras et al., "Design, Synthesis, and Structure-Activity Relationships of a Series of 3-[2-(1-Benzylpiperidin-4-yl)ethylamino]pyridazine Derivatives as Acetylcholinesterase Inhibitors," J. Med. Chem., 44:2707-2718 (2001).

Coppola et al., "Pyrimidones. 2. Synthesis and Reactions of 2-Chloropyrimidines," J. Heterocyclic Chemistry, 17:1479-1482 (1980).

Database Beilstein, Beilstein Institut zur Foerderung der Chemischen Wissenschaften, DE; 5688187 BRN 4807006 1989, XP002355796 abstract.

Database Beilstein, Beilstein Institut zur Foerderung der Chemischen Wissenschaften, DE; BRN 4182175 1991, XP002355796 abstract.

Database Beilstein, Beilstein Institut zur Foerderung der Chemischen Wissenschaften, DE; BRN 4870130 1991, XP002355793 abstract.

Database Beilstein, Beilstein Institut zur Foerderung der Chemischen Wissenschaften, DE; BRN 6398075 1988, XP002355794 abstract.

Eguchi et al., "Studies on Antiatherosclerotic Agents. Synthesis and Inhibitory Activities on Platelet Aggregation of 4-Aryl Derivatives of 7-Ethoxycarbonyl-6,8-dimethyl-1(2H)-phthalazinone," Chemical & Pharmaceutical Bulletin, 39(8):2009-2015 (1991).

Giannangeli et al., "Effect of Modifications of the Alkylpiperazine Moiety of Trazodone on 5HT2A and alpha1 Receptor Binding Affinity," J. Med. Chem., 42:336-345 (1999).

Guery et al., "Synthesis of 4-Aryl-1-(4-methylpiperazin-1-yl)phthalazines by Suzuki-type Cross-coupling Reaction," Synthesis, No. 5:699-701 (2001).

Guillory, "Generation of Polymorphs, Hydrates, Solvates, and Amorphous Solids," in: Polymorphism in Pharmaceutical Solids, Harry G. Brittain, Ed., Chapter 5, pp. 183-226 (1999).

Haider et al., "Product Class 10: Phthalazines," in: Science of Synthesis: Houben-Weyle Methods of Molecular Transformations, Y. Yamamoto, Ed., Georg Thieme Verlag, Stuttgart, pp. 315-372 (2004).

Hancock, "The challenge of drug discovery of a GPCR target: Analysis of preclinical pharmacology of histamine H3 antagonists/inverse agonists," Biochemical Pharmacology, 71:1103-1113 (2006).

Haugwitz et al., "Antiparasitic Agents. 5. Synthesis and Anthelminitic Activities of Novel 2-Heteroaromatic-Substituted Isothiocyanatobenzoxazoles and Benzonthiazoles," J. Med. Chem., 25:969-974 (1982).

Hori et al., "Novel 4-substituted 2-piperazinylquinazolines as potent anticonvulsive and antihypoxic agents," Chemical & Pharmaceutical Bulletin, 38(5):1286-1291 (1990) (abstract only).

Hori et al., "Potential nootropic agents, 4-alkoxy-2-(1-piperazinyl)quinazaline derivatives," Chemical & Pharmaceutical Bulletin, 39(2):367-371 (1991) (abstract only).

Hu et al., "Development of a novel therapeutic suppressor of brain proinflammatory cytokine up-regulation that attenuates synaptic dysfunction and behavioral deficits," Bioorganic & Medicinal Chemistry Letters 17, pp. 414-418 (2007).

International Search Report and Written Opinion for related PCT Application No. PCT/EP2007/054940, mailed Oct. 25, 2007.

Kawaguchi et al., "Parallel dose-response studies of the voltage-dependent Na+ channel antagonist BW619C89, and the voltage-dependent Ca2+ channel antagonist nimodioine, in rat transient focal cerebral ischaemia," Eur. J. Pharm., 364:99-105 (1999).

Klauschenz et al., "Synthesis and cardiotonic activity of 6-substituted 5-cyano-(3,4'-bipyridine)-1'oxides and related compounds: molecular structure of 5-cyano-6-morpholino-(3,4'-bipyridine)-1'-oxide (AWD 122-239)," Eur. J. Med. Chem., 29:175-184 (1994).

Leurs et al., "The Histamine H3 Receptor: from Gene Cloning to H3 Receptor Drugs," Nature Reviews/Drug Discovery, 4:107-120 (2005).

Leurs et al., "The medicinal chemistry and therapeutic potentials of ligands of the histamine H3 receptor," in Progress in Drug Research, Ernst Jucker, Ed., 45:107-165 (1995).

Leurs et al., "Therapeutic potential of histamine H3 receptor agonists and antagonists," Trends in Pharmacological Sciences, 19(5):177-183 (1998).

Levay et al., "Correlation of the Chemical Reactivity of Some Tetrazine Derivatives with Their Reactivity toward Ortho-positronium Atoms and Their LUMO Energies," J. Phys. Chem. A, 108:1753-1756 (2004).

Linney et al., "Design, Synthesis, and Structure-Activity Relationships of Novel Non-Imidazole Histamine H3 Receptor Antagonists," J. Med. Chem., 43:2362-2370 (2000).

Lumma, Jr. et al., "Piperazinylpyrazines with Central Serotoninmimetic Activity," J. Med. Chem., 21(6):536-542 (1978).

Mackins et al., "Therapeutic potential of H3-receptor agonists in myocardial infarction," Expert Opinion on Investigational Drugs, 9(11):2537-2542 (2000).

Malmlof et al., "Targeting of the Central Histaminergic System for Treatment of Obesity and Associated Metabolic Disorders," Drug Development Research, 67:651-665 (2006).

Mazarguil et al., "Enamines of N-methyl- and N-phenylpiperazine. I. Synthesis and physicochemical study," Bulletin de La Societe Chimique de France, 1:319-324 (1969) (abstract only).

McIntyre et al., "Pyradazine Based Inhibitors of p38 MAPK," Bioorganic & Medicinal Chemistry Letters, 12:689-692 (2002).

McLeod et al., "Sch 50971, an Orally Active Histamine H3 Receptor Agonist, Inhibits Central Neurogenic Vascular Inflammation and Produces Sedation in the Guinea Pig," J. Pharmacol. Exp. Ther., 287(1):43-50 (1998).

Mokrosz et al., "Structure-Activity Relationship Studies of Central Nervous System Agents. 5. Effect of the Hydrocarbon Chain on the Affinity of 4-Substituted 1-(3-Chlorophenyl)piperazines for 5-HT1A Receptor Site," J. Med. Chem., 35:2369-2374 (1992).

Morisset et al., "High constitutive activity of native H3 receptors regulates histamine neurons in brain," Nature, 408:860-864 (2000).

Parrot et al., "Synthesis of Substituted 3-Amino-6-arylpyridazines via Suzuki Reaction," Synthesis, No. 7, pp. 1163-1168 (1999).

Prasad et al., "Potential Antihypertensive Agents. II. Unsymmetrically 1,4-Disubstituted Piperazines," J. Med. Chem., 11:1144-1150 (1968).

Refaat et al., "Synthesis and Antidepressant Activity of Novel Pyridazine Derivatives," Bulletin of the Faculty of Pharmacy, Cairo University, 42(2):415-423 (2004).

Rival et al., "5-HT3 Antagonists Derived from Aminopyridazine-type Muscarinic M1 Agonists," J. Med. Chem., 41(3):311-317 (1998).

Rodriguez-Spong et al., "General principles of pharmaceutical solid polymorphism: a supramolecular perspective," Advanced Drug Delivery Reviews, 56:241-274 (2004).

Rohet et al., "Synthesis and Analgesic Effects of 3-Substituted 4,6-Diarylpyridazine Derivatives of the Arylpiperazine Class," Bioorganic & Medicinal Chemistry, 5(4):655-659 (1997).

Stark et al., "Development of histamine H3-receptor antagonists," Drugs of the Future, 21(5):507-520 (1996).

Steck et al., "Pyridazines VIII. Some 6-Aryl-3-(basically-substituted) Pyridazines," J. of Heterocyclic Chemistry, 12:1009-1013 (1975).

Tafesse et al., "Synthesis and evaluation of pyridazinylpiperazines as vanilloid receptor 1 antagonists," Bioorganic & Medicinal Chemistry Letters, 14:5513-5519 (2004).

Tamayo et al., "Design and synthesis of potent pyridazine inhibitors of p38 MAP kinase," Bioorganis & Medicinal Chemistry Letters, 15:2409-2413 (2005).

Tozer et al., "Histamine H3 receptor antagonists," Expert Opinion on Therapeutic Patents, 10(7):1045-1055 (2000).

Werbel et al., "Synthesis and Antimalarial Effects of N,N-Dialkyl-6-(substituted phenyl)-1,2,4,5-tetrazin-3-amines," J. of Heterocyclic Chemistry, 16:881-894 (1979).

Wu et al., "Synthesis and platelet aggregation activity of 6-[4-substituted-piperazinyl)phenyl]-4,5-dihydro-3(2H)-pyridazinones," Zhongguo Yaowu Huaxue Zazhi Bianjibu, 9(3):172-175, 185 (1999) (abstract only).

Xu et al., "Studies on synthesis and anticonvulant activity of 3-substituted piperazino-6-(substituted-phenyl) pyridazines," Journal of Beijing Medical University, 23(6):477-480 (1991).

Xu et al., "Synthesis and anticonvulsant activity of 6-aryl-3-(4-methylpiperazine) pyridazine compounds," Chinese Journal of Medicinal Chemistry 1(1):42-48 (1990).

Zaragoza et al., "2-(4-Alkylpiperazin-1-yl)quinolines as a New Class of Imidazole-Free Histamine H3 Receptor Antagonists," Journal of Medicinal Chemistry, 48(1):306-311 (2005).

Falorni et al., "Chiral Ligands Containing Heteroatoms. 7. An Investigation on the Stereochemistry of the Ketone Reductions by Chiral Diamines/Tin Hydride Systems.," Tetrahedron: Asymmetry 2(4):287-298 (1991).

Ganellin et al., "Synthesis of Potent Non-imidazole Histamine H3-Receptor Antagonists," Arch. Pharm. Pharm. Med. Chem., 331:395-404 (1998).

Mazarguil et al., "Enamines of N-methyl and N-phenylpiperazines. Synthesis of unsymmetrical N,N'-disubstituted and N-monosubstituted piperazines," Sciences Chimique, 267(12):724-727 (1968) (abstract only).

Mir et al., "Nucleophilic Substitution Reactions of Heterocyclic Amines and Acyclic Diamines with Chlorofluorooelefins and Hexafluoropropylene Oxide," J. Org. Chem. 59:173-177 (1994).

Walczynski et al., "Non-Imidazole Histamine H3 Ligands, Part 2: New 2-Substituted Benzothiazoles as Histamine H3 Antagonists," Arch. Pharm. Pharm. Med. Chem., 332:389-398 (1999).

Walczynski et al., "Non-imidazole histamine H3 ligands. Part I. Synthesis of 2-(1-piperazinyl)- and 2-(hexahydro-1H-1,4-diazepin-1-yl)benzothiazole derivatives as H3-antagonists with H1 blocking activities," Il Farmaco 54:684-694 (1999).

Walczynski et al., "Non-imidazole histamine H3 ligands. Part III. New 4-n-propylpiperazines as non-imidazole histamine H3-antagonists," European Journal of Medicinal Chemistry, 40:15-23 (2005).

* cited by examiner

3-(1,3-BENZODIOXOL-5-YL)-6-(4-CYCLO-PROPYLPIPERAZIN-1-YL)-PYRIDAZINE, ITS SALTS AND SOLVATES AND ITS USE AS HISTAMINE H3 RECEPTOR ANTAGONIST

CROSS-REFERENCE TO RELATED APPLICATIONS

The present application is a United States national stage application, pursuant to 35 U.S.C. 371, of PCT application No. PCT/EP2007/054940, filed May 22, 2007 and published as WO 2007/137968, which in turn claims the benefit of priority to European Patent Application No. 06114615.5, filed May 29, 2006, and European Patent Application No. 06120117.4, filed Sep. 5, 2006.

FIELD OF THIS INVENTION

The present invention relates to novel compounds being histamine H3 receptor antagonists, to the use of these compounds in pharmaceutical compositions, to pharmaceutical compositions comprising the compounds, and to methods of treatment employing these compounds or compositions. The present compounds show a high and selective binding affinity for the histamine H3 receptor, indicating histamine H3 receptor antagonistic, inverse agonistic or agonistic activity. As a result, the compounds are useful for the treatment of diseases or disorders related to the histamine H3 receptor.

BACKGROUND OF THIS INVENTION

The existence of the histamine H3 receptor has been known for several years and the receptor is of current interest for the development of new medicaments (see, for example, *Drugs Fut* 1996; 21: 507-20; *Progress in Drug Research* 1995; 45: 107-65). The human histamine H3 receptor has been cloned, cf. *Molecular Pharmacology*, 1999; 55: 1101-7. The histamine H3 receptor is a presynaptic autoreceptor located mainly in the central nervous system. Recent evidence suggests that the H3 receptor shows intrinsic, constitutive activity, in vitro as well as in vivo (i.e., it is active in the absence of an agonist; see, for example, *Nature* 2000; 408: 860-4). Compounds acting as inverse agonists can inhibit this activity. The histamine H3 receptor has been demonstrated to regulate the release of histamine and also of other neurotransmitters such as serotonin and acetylcholine. A histamine H3 receptor antagonist or inverse agonist would therefore be expected to increase the release of these neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists and antagonists could be important mediators of neuronal activity. Accordingly, the histamine H3 receptor is an important target for new therapeutics.

Several publications disclose the preparation and use of histamine H3 agonists and antagonists. Some of these are imidazole derivatives (see, for example, *Drugs Fut* 1996; 21: 507-20; *Expert Opinion on Therapeutic Patents* 2000; 10: 1045-55). However, a variety of imidazole-free ligands of the histamine H3 receptor is also described (see, for example, *Arch Pharm Pharm Med Chem* 1999; 332: 389-98; *J Med Chem* 2000; 43: 2362-70; *Arch Pharm Pharm Med Chem* 1998; 331: 395-404; *Il Farmaco* 1999; 54: 684-94; WO 99/42458, EP 0 978 512, WO 97/17345, U.S. Pat. No. 6,316,475, WO 01/66534, WO 01/74810, WO 01/44191, WO 01/74815, WO 01/74773, WO 01/74813, WO 01/74814 and WO 02/12190. The state of the art is also reviewed in *Drug Discovery Today*, 2005; 10: 1613-17; *Nat Rev Drug Discov*, 2005; 4: 107, and *Drug Dev Res*, 2006, 67: 651-665. In view of the art's interest in histamine H3 receptor agonists, inverse agonists and antagonists, novel compounds which interact with the histamine H3 receptor would be a highly desirable contribution to the art.

In WO 03/066604, 3-(4-cyclopropylpiperazin-1-yl)-6-(3,4-dimethoxyphenyl)pyridazine hydrochloride is mentioned in Example 127.

OBJECTS OF THIS INVENTION

One object of this invention is to furnish compounds having a reducing effect on the intake of food.

A further object of this invention is to furnish compounds which can be used for the reduction of weight.

A further object of this invention is to furnish compounds which can be used for the treatment of overweight or obesity.

A further object of this invention is to furnish compounds which can be used for the suppression of appetite or for satiety induction.

A further object of this invention is to furnish compounds which can be used for the treatment of type 2 diabetes.

A further object of this invention is to furnish compounds which can be used to cure or prevent other of the diseases or pharmacological conditions mentioned below.

A further object of this invention is to furnish compounds which fulfil the general requirements to a medicament, such as non-toxicity, non-mutagenicity and absence of adverse events after administration to humans.

A further object of this invention is to overcome or ameliorate at least one of the disadvantages of the prior art, or to provide a useful alternative.

DEFINITIONS

In the structural formulae given herein and throughout the present specification, the following terms have the indicated meaning:

The term "solvate" as used herein is a complex of defined stoichiometry formed by a solute (in casu, a compound according to the present invention) and a solvent. Solvents are those commonly used in the pharmaceutical art, by way of example, water, ethanol, acetic acid, and the like. The term "hydrate" refers to the complex where the solvent molecule is water.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

The terms "disease", "condition" and "disorder" as used herein are used interchangeably to specify a state of a patient which is not the normal physiological state of man.

The term "medicament" as used herein means a pharmaceutical composition suitable for administration of the pharmaceutically active compound to a patient.

The term "prodrug" as used herein includes biohydrolyzable amides and biohydrolyzable esters and also encompasses a) compounds in which the biohydrolyzable functionality in such a prodrug is encompassed in the compound according to the present invention, and b) compounds which may be oxidized or reduced biologically at a given functional group to yield drug substances according to the present invention. Examples of these functional groups include 1,4-dihydropyridine, N-alkyl-carbonyl-1,4-dihydropyridine, 1,4-cyclohexadiene, tert-butyl, and the like.

The term "biohydrolyzable ester" as used herein is an ester of a drug substance (in this invention, a compound of formula I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) in plasma. Many examples of such are known in the art and include by way of example lower alkyl esters (for example, $C_{1-4}$-alkyl esters), lower acyloxyalkyl esters, lower alkoxyacyloxyalkyl esters, alkoxyacyloxy esters, alkyl acylamino alkyl esters, and choline esters.

The term "biohydrolyzable amide" as used herein is an amide of a drug substance (in this invention, a compound of general formula I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

The term "pharmaceutically acceptable" as used herein means suited for normal pharmaceutical applications, i.e. giving rise to no adverse events in patients etc.

The term "effective amount" as used herein means a dosage which is sufficient in order for the treatment of the patient to be effective compared with no treatment.

The term "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

The term "metabolite" as used herein is any intermediate or product resulting from metabolism.

The term "metabolism" as used herein refer to the biotransformation of a drug substance (in this invention, a compound of general formula I) administered to a patient.

The representative examples mentioned above are specific embodiments of this invention.

SUMMARY OF THIS INVENTION

The invention relates to compounds mentioned in the claims below. The compounds of this invention differ structurally from the known compounds.

Due to their interaction with the histamine H3 receptor, compounds of this invention are useful in the treatment of a wide range of conditions and disorders in which an interaction with the histamine H3 receptor is beneficial. Thus, the compounds may find use, for example, in the treatment of diseases of the central nervous system and in the peripheral nervous system.

The invention also relates to the use of said compounds in therapy, and in particular to pharmaceutical compositions comprising said compounds.

In another embodiment, the invention relates to methods of treatment, the method comprising administering to a subject in need thereof an effective amount of a compound claimed herein.

In a still further embodiment, the invention relates to the use of compounds claimed herein in the manufacture of medicaments.

DESCRIPTION OF THE PREFERRED EMBODIMENTS

Due to their interaction with the histamine H3 receptor, the compounds of this invention as defined in the claims below and elsewhere in this specification are useful in the treatment of a wide range of conditions and disorders in which an interaction with the histamine H3 receptor is beneficial. Thus, the compounds may find use, for example, in the treatment of diseases of the central nervous system and in the peripheral nervous system.

The compounds of the present invention interact with the histamine H3 receptor and are accordingly particularly useful in the treatment of a variety of diseases or conditions in which histamine H3 interactions are beneficial.

In one aspect, the invention provides the use of a compound as claimed herein in a pharmaceutical composition. The pharmaceutical composition may in another aspect of the invention comprise, as an active ingredient, at least one compound as claimed herein together with one or more pharmaceutically acceptable carriers or excipients. In another aspect, the invention provides such a pharmaceutical composition in unit dosage form, comprising from about 0.05 mg to about 1000 mg, for example, from about 0.1 mg to about 500 mg, such as from about 0.5 mg to about 200 mg of a compound claimed herein.

In another aspect, the invention provides the use of a compound claimed herein for the preparation of a pharmaceutical composition for the treatment of diseases and disorders in which an inhibition of the H3 histamine receptor has a beneficial effect.

In another aspect, the invention provides the use of a compound claimed herein for the preparation of a pharmaceutical composition having histamine H3 antagonistic activity or histamine H3 inverse agonistic activity.

In another aspect the invention provides the use of a compound claimed herein for the preparation of a pharmaceutical composition for the reduction of weight.

In another aspect, the invention provides the use of a compound claimed herein for the preparation of a pharmaceutical composition for the treatment of overweight or obesity.

In another aspect, the invention provides the use of a compound claimed herein for the preparation of a pharmaceutical composition for the suppression of appetite or for satiety induction.

In another aspect, the invention provides the use of a compound claimed herein for the preparation of a pharmaceutical composition for the prevention and/or treatment of disorders and diseases related to overweight or obesity, such as dyslipidaemia, coronary heart disease, gallbladder disease, osteoarthritis and various types of cancer such as endometrial, breast, prostate and colon cancers.

In another aspect, the invention provides the use of a compound claimed herein for the preparation of a pharmaceutical composition for the prevention and/or treatment of eating disorders, such as bulimia or binge eating.

In another aspect, the invention provides the use of a compound claimed herein for the preparation of a pharmaceutical composition for the treatment of IGT (Impaired glucose tolerance).

In another aspect, the invention provides the use of a compound claimed herein for the preparation of a pharmaceutical composition for the treatment of type 2 diabetes.

In another aspect, the invention provides the use of a compound claimed herein for the preparation of a pharmaceutical composition for the delaying or prevention of the progression from IGT to type 2 diabetes.

In another aspect, the invention provides the use of a compound claimed herein for the preparation of a pharmaceutical composition for the delaying or prevention of the progression from non-insulin requiring type 2 diabetes to insulin requiring type 2 diabetes.

In another aspect, the invention provides the use of a compound claimed herein for the preparation of a pharmaceutical composition for the treatment of diseases and disorders in which a stimulation of the H3 histamine receptor has a beneficial effect.

In another aspect, the invention provides the use of a compound claimed herein for the preparation of a pharmaceutical composition having histamine H3 agonistic activity.

In another aspect, the invention provides the use of a compound claimed herein for the preparation of a pharmaceutical composition for the treatment of allergic rhinitis, ulcer or anorexia.

In another aspect, the invention provides the use of a compound claimed herein for the preparation of a pharmaceutical composition for the treatment of Alzheimer's disease, narcolepsy, attention deficit disorders or reduced wakefulness, or for the regulation of sleep.

In another aspect, the invention relates to the use of a compound claimed herein for the preparation of a pharmaceutical preparation for the treatment of airway disorders, such as asthma, for regulation of gastric acid secretion, or for treatment of diarrhoea.

In another aspect, the invention provides a method for the treatment of disorders or diseases related to the H3 histamine receptor, the method comprising administering to a subject in need thereof an effective amount of a compound claimed herein, or of a pharmaceutical composition comprising such a compound.

In another aspect, the invention provides a method as described above, wherein the effective amount of a compound claimed herein is in the range of from about 0.05 mg to about 2000 mg, preferably from about 0.1 mg to about 1000 mg, and more preferably from about 0.5 mg to about 500 mg per day.

In one aspect, the invention relates to compounds which exhibit histamine H3 receptor antagonistic activity or inverse agonistic activity and which may accordingly be useful in the treatment of a wide range of conditions and disorders in which histamine H3 receptor blockade is beneficial.

In another aspect, the invention provides a method for reduction of weight, the method comprising administering to a subject in need thereof an effective amount of a compound claimed herein.

In another aspect, the invention provides a method for treatment of overweight or obesity, the method comprising administering to a subject in need thereof an effective amount of a compound claimed herein.

In another aspect, the invention provides a method for suppression of appetite or for satiety induction, the method comprising administering to a subject in need thereof an effective amount of a compound claimed herein.

In another aspect, the invention provides a method for prevention and/or treatment of disorders or diseases related to overweight or obesity, such as dyslipidaemia, coronary heart disease, gallbladder disease, osteoarthritis and various types of cancer, for example, endometrial, breast, prostate or colon cancer, the method comprising administering to a subject in need thereof an effective amount of a compound claimed herein.

In another aspect, the invention provides a method for prevention and/or treatment of eating disorders, such as bulimia and binge eating, the method comprising administering to a subject in need thereof an effective amount of a compound claimed herein.

In another aspect, the invention provides a method for the treatment of IGT (Impaired glucose tolerance), the method comprising administering to a subject in need thereof an effective amount of a compound claimed herein.

In another aspect, the invention provides a method for the treatment of type 2 diabetes, the method comprising administering to a subject in need thereof an effective amount of a compound claimed herein.

In another aspect, the invention provides a method for the delaying or prevention of the progression from IGT to type 2 diabetes, the method comprising administering to a subject in need thereof an effective amount of a compound claimed herein.

In another aspect, the invention provides a method for the delaying or prevention of the progression from non-insulin requiring type 2 diabetes to insulin requiring type 2 diabetes, the method comprising administering to a subject in need thereof an effective amount of a compound claimed herein.

In another aspect, the invention relates to compounds which exhibit histamine H3 receptor agonistic activity and which may accordingly be useful in the treatment of a wide range of conditions and disorders in which histamine H3 receptor activation is beneficial.

Compounds of the present invention may also be used for the treatment of airway disorders (such as asthma), as anti-diarrhoeals, and for the modulation of gastric acid secretion.

Furthermore, compounds of the present invention may be used for the treatment of diseases associated with the regulation of sleep and wakefulness, and for the treatment of narcolepsy and attention deficit disorders.

Moreover, compounds of the invention may be used as CNS stimulants or as sedatives.

The present compounds may also be used for the treatment of conditions associated with epilepsy. Additionally, compounds of the invention may be used for the treatment of motion sickness and vertigo. Furthermore, they may be useful as regulators of hypothalamo-hypophyseal secretion, as antidepressants, as modulators of cerebral circulation, and in the treatment of irritable bowel syndrome.

Further, compounds of the present invention may be used for the treatment of dementia and Alzheimer's disease.

Compounds of the present invention may also be useful for the treatment of allergic rhinitis, ulcer or anorexia.

Compounds of the present invention may furthermore be useful for the treatment of migraine (see, for example, *The Journal of Pharmacology and Experimental Therapeutics* 1998; 287: 43-50) and for the treatment of myocardial infarction (see *Expert Opinion on Investigational Drugs* 2000; 9: 2537-42).

In a further aspect of the invention, treatment of a patient with a compound of the present invention is combined with diet and/or exercise.

In a further aspect of the invention, one of more a compound claimed herein is/are administered in combination with one or more further active substances in any suitable ratio(s). Such further active agents may, for example, be selected from antiobesity agents, antidiabetics, antidyslipidemic agents, antihypertensive agents, agents for the treatment of complications resulting from or associated with diabetes, and agents for the treatment of complications and disorders resulting from or associated with obesity.

Thus, in a further aspect of this invention, a compound claimed herein may be administered in combination with one or more antiobesity agents or appetite regulating agents. Such agents may, for example, be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, opioid antagonists (such as naltrexone), exendin-4, GLP-1 and ciliary neurotrophic factor.

In one embodiment of the invention, an antiobesity agent administered in combination with one or more compounds of the invention is leptin.

In another embodiment, such an antiobesity agent is dexamphetamine or amphetamine.

In another embodiment, such an antiobesity agent is fenfluramine or dexfenfluramine.

In still another embodiment, such an antiobesity agent is sibutramine.

In a further embodiment, such an antiobesity agent is orlistat.

In another embodiment, such an antiobesity agent is mazindol or phentermine.

In still another embodiment, such an antiobesity agent is phendimetrazine, diethylpropion, fluoxetine, bupropion, topiramate or ecopipam.

In yet a further aspect of the invention, a compound claimed herein may be administered in combination with one or more antidiabetic agents. Relevant antidiabetic agents include insulin, insulin analogues and derivatives such as those disclosed in EP 0 792 290 (Novo Nordisk A/S), for example, $N^{\epsilon B29}$-tetradecanoyl des(B30) human insulin, EP 0 214 826 and EP 0 705 275 (Novo Nordisk A/S), for example, $Asp^{B28}$ human insulin, U.S. Pat. No. 5,504,188 (Eli Lilly), for example, $Lys^{B28}$ $Pro^{B29}$ human insulin, EP 0 368 187 (Aventis), for example, Lantus®, all of which are incorporated herein by reference, GLP-1 derivatives, such as those disclosed in WO 98/08871 (Novo Nordisk A/S), incorporated herein by reference, as well as orally active hypoglycaemic agents.

The orally active hypoglycaemic agents preferably comprise imidazolines, sulfonylureas, biguanides, meglitinides, oxadiazolidinediones, thiazolidinediones, insulin sensitizers, α-glucosidase inhibitors, agents acting on the ATP-dependent potassium channel of the β-cells, for example, potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists, such as one of those disclosed in WO 99/01423 and WO 00/39088 (Novo Nordisk A/S and Agouron Pharmaceuticals, Inc.), both of which are incorporated herein by reference, GLP-1 agonists, such as those disclosed in WO 00/42026 (Novo Nordisk A/S and Agouron Pharmaceuticals, Inc.), incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antilipidemic agents, compounds lowering food intake, PPAR (peroxisome proliferator-activated receptor) and RXR (retinoid X receptor) agonists, such as ALRT-268, LG-1268 or LG-1069.

In one embodiment of the invention, a compound claimed herein may be administered in combination with insulin or an insulin analogue or derivative, such as $N^{\epsilon B29}$-tetradecanoyl des(B30) human insulin, $Asp^{B28}$ human insulin, $Lys^{B28}$ $Pro^{B29}$ human insulin, Lantus®, or a mix-preparation comprising one or more of these.

In a further embodiment of the invention, one or a compound claimed herein may be administered in combination with a sulfonylurea, for example, tolbutamide, chlorpropamide, tolazamide, glibenclamide, glipizide, glimepiride, glicazide or glyburide.

In another embodiment of the invention, a compound claimed herein may be administered in combination with a biguanide, for example, metformin.

In yet another embodiment of the invention, a compound claimed herein may be administered in combination with a meglitinide, for example, repaglinide or nateglinide.

In still another embodiment of the invention, a compound claimed herein may be administered in combination with a thiazolidinedione insulin sensitizer, for example, troglitazone, ciglitazone, pioglitazone, rosiglitazone, isaglitazone, darglitazone, englitazone, CS-011/CI-1037 or T 174, or a compound disclosed in WO 97/41097, WO 97/41119, WO 97/41120, WO 00/41121 and WO 98/45292, all of which are incorporated herein by reference.

In still another embodiment of the invention, a compound claimed herein may be administered in combination with an insulin sensitizer, for example, such as GI 262570, YM-440, MCC-555, JTT-501, AR-H039242, KRP-297, GW-409544, CRE-16336, AR-H049020, LY510929, MBX-102, CLX-0940, GW-501516, or a compound disclosed in WO 99/19313, WO 00/50414, WO 00/63191, WO 00/63192, WO 00/63193, WO 00/23425, WO 00/23415, WO 00/23451, WO 00/23445, WO 00/23417, WO 00/23416, WO 00/63153, WO 00/63196, WO 00/63209, WO 00/63190 or WO 00/63189 (Novo Nordisk A/S), all of which are incorporated herein by reference.

In a further embodiment of the invention, a compound claimed herein may be administered in combination with an α-glucosidase inhibitor, for example, voglibose, emiglitate, miglitol or acarbose.

In another embodiment of the invention, a compound claimed herein may be administered in combination with an agent acting on the ATP-dependent potassium channel of the β-cells, for example, tolbutamide, glibenclamide, glipizide, glicazide, BTS-67582 or repaglinide.

In yet another embodiment of the invention, a compound claimed herein may be administered in combination with nateglinide.

In still another embodiment, a compound claimed herein may be administered in combination with an antihyperlipidemic agent or antilipidemic agent, for example, cholestyramine, colestipol, clofibrate, gemfibrozil, lovastatin, pravastatin, simvastatin, probucol or dextrothyroxine.

In still another embodiment of the invention, a compound claimed herein may be administered in combination with an antilipidemic agent, for example, cholestyramine, colestipol, clofibrate, gemfibrozil, lovastatin, pravastatin, simvastatin, probucol or dextrothyroxine.

In another aspect of the invention, a compound claimed herein may be administered in combination with more than one of the above-mentioned compounds, for example, in combination with metformin and a sulfonylurea such as glyburide; a sulfonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Furthermore, a compound claimed herein may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: *The Science and Practice of Pharmacy*, 19$^{th}$ Edition, Gennaro, Ed., Mack Publishing Co., Easton, Pa., 1995.

It should be understood that any suitable combination of compounds according to the invention with diet and/or exercise, one or more of the above-mentioned compounds and optionally one or more other active substances are considered to be within the scope of the present invention.

The compounds of the present invention may be chiral, and it is intended that any enantiomers, as separated, pure or partially purified enantiomers or racemic mixtures thereof are included within the scope of the invention.

Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention.

Furthermore, some of the compounds of the present invention may exist in different tautomeric forms and it is intended that any tautomeric forms, which the compounds are able to form, are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in *J Pharm Sci* 1977; 66: 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Also intended as pharmaceutically acceptable acid addition salts are the hydrates which the present compounds are able to form.

The acid addition salts may be obtained as the direct products of compound synthesis. Alternatively, the free base may be dissolved in a suitable solvent containing the appropriate acid, and the salt isolated by evaporating the solvent or otherwise separating the salt and solvent.

Compounds of the present invention may form solvates with standard low molecular weight solvents using methods well known to the person skilled in the art. Such solvates are also to be understood as being within the scope of the present invention.

The invention also encompasses prodrugs of the present compounds which following administration undergo chemical conversion by metabolic processes before becoming active pharmacological substances. In general, such prodrugs will be functional derivatives of the present compounds which are readily convertible in vivo into the required compound of the formula I. Conventional procedures for the selection and preparation of suitable prodrug derivatives are described, for example, in *Design of Prodrugs*, ed.: H. Bundgaard, Elsevier, 1985.

This invention also encompasses active metabolites of the present compounds.

Combining one or more of the individual embodiments described herein, optionally also with one or more of the individual claims below, results in further embodiments and the present invention relates to all possible combinations of said embodiments and claims.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques, such as those disclosed in Remington: *The Science and Practice of Pharmacy*, 19$^{th}$ Edition, Gennaro, Ed., Mack Publishing Co., Easton, Pa., 1995.

The pharmaceutical compositions may be specifically formulated for administration by any suitable route, such as the oral, rectal, nasal, pulmonary, topical (including buccal and sublingual), transdermal, intracisternal, intraperitoneal, vaginal or parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings, such as enteric coatings, or they can be formulated so as to provide controlled release of the active ingredient, such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also to be understood as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferably from about 0.05 to about 10 mg/kg body weight per day, administered in one or more doses, such as from 1 to 3 doses. The exact dosage will depend upon the frequency and mode of administration, the sex, age, weight and general condition of the subject treated, the nature and severity of the condition treated and any concomitant diseases to be treated, and other factors evident to those skilled in the art.

The formulations may conveniently be presented in unit dosage form by methods known to those skilled in the art. A typical unit dosage form for oral administration one or more times per day, such as from 1 to 3 times per day, may contain from 0.05 to about 1000 mg, preferably from about 0.1 to about 500 mg, and more preferably from about 0.5 mg to about 200 mg of a compound (or a salt or other derivative thereof as set forth above), according to the invention.

For parenteral routes, such as intravenous, intrathecal, intramuscular and similar administration, typical doses are of the order of about half the dose employed for oral administration.

The compounds of this invention are generally utilized as the free substance or as a pharmaceutically acceptable salt thereof. One example is an acid addition salt of a compound having a free base functionality. When a compound of the formula I contains a free base functionality, such salts are prepared in a conventional manner by treating a solution or suspension of the free base form of a compound claimed herein with a chemical equivalent (acid-base equivalent) of a pharmaceutically acceptable acid. Representative examples of relevant inorganic and organic acids are mentioned above. Physiologically acceptable salts of a compound of the invention having a hydroxy group include the anion of said compound in combination with a suitable cation, such as sodium or ammonium ion.

For parenteral administration, solutions of the novel compounds of the formula I in sterile aqueous solution, aqueous propylene glycol or sesame or peanut oil may be employed. Such aqueous solutions should be suitably buffered if necessary, and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylenes or water. Similarly, the carrier or diluent may include any sustained release material known in the art, such as glyceryl monostearate or glyceryl distearate, alone or mixed with a wax. The pharmaceutical compositions formed by combining the novel compounds of the formula I and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier may vary widely, but will usually be from about 25 mg to about 1 g. If a liquid carrier is used, the preparation may be in the form of a syrup, emulsion, soft gelatine capsule or sterile injectable liquid, such as an aqueous or non-aqueous liquid suspension or solution.

A typical tablet, which may be prepared by conventional tabletting techniques, may in the core contain 5.0 mg of a compound of the invention, 67.8 mg of lactosum Ph. Eur., 31.4 mg of cellulose, microcrystalline (Avicel), 1.0 mg of Amberlite®IRP88 (i.e., Polacrillin potassium NF, tablet disintegrant, Rohm and Haas) and magnesii stearas Ph. Eur. q.s. with a coating of approximately 9 mg of hydroxypropyl methylcellulose and approximately 0.9 mg of Mywacett 9-40 T (being acylated monoglyceride used as plasticizer for film coating).

If desired, the pharmaceutical composition of this invention may comprise the compound of the formula I in combination with one or more further pharmacologically active substances, for example, substances chosen among those described in the foregoing.

Briefly, the compounds of this invention can be prepared in a manner known per se or analogous with known processes.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (for example, "such as") provided herein, is intended merely to better illuminate the invention and does not pose a limitation on the scope of the invention unless otherwise claimed.

No language in the specification should be construed as indicating any non-claimed element as essential to the practice of the invention.

The citation and incorporation of patent documents herein is done for convenience only and does not reflect any view of the validity, patentability, and/or enforceability of such patent documents. The mentioning herein of references is no admission that they constitute prior art.

Herein, the word "comprise" is to be interpreted broadly meaning "include", "contain" or "comprehend" (vide, EPO's guidelines C 4.13).

This invention includes all modifications and equivalents of the subject matter recited in the claims appended hereto as permitted by applicable law.

The following examples are offered by way of illustration, not by limitation.

EXAMPLES

In the example below, the following terms are intended to have the following, general meanings: h is hour(s), kD is kiloDalton(s), L is liter(s), M is molar, mg is milligram(s), min is minute(s), mL is milliliter(s), mM is millimolar, mmol is millimole(s), mol is mole(s), N is normal, NMR is nuclear magnetic resonance spectroscopy, DMSO is dimethylsulfoxide, THF is tetrahydrofuran, CDCl$_3$ is deuterio chloroform, and DMSO-d$_6$ is hexadeuterio dimethylsulfoxide.

Briefly, the compounds of this invention can be prepared in a manner known perse or analogous with known processes.

NMR spectra were recorded on a Bruker 300 or 400 MHz spectrometer. Shifts (δ) are given in parts per million (ppm) down field from tetramethylsilane as internal reference standard.

Example 1

3-(1,3-Benzodioxol-5-yl)-6-(4-cyclopropylpiperazin-1-yl)pyridazine dihydrochloride

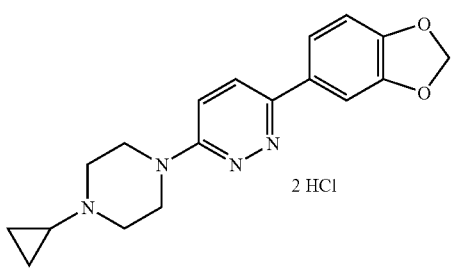 [SMILES: c1cc2c(cc1-c1ccc(N3CCN(C4CC4)CC3)nn1)OCO2 ; "2 HCl"]

Step 1

3-Chloro-6-piperazin-1-ylpyridazine

Piperazine (20.0 g, 232 mmol) and 3,6-dichloropyridazine (34.6 g, 232 mmol) were mixed with 2-butanone and heated at 62° C. for 16 h. The reaction mixture was cooled to room temperature and the precipitated product filtered and washed with 2-butanone. The solid was redissolved in DCM (250 mL), filtered and the filtrate evaporated. The solid was dried in vacuo to yield 37.3 g, 81% 3-chloro-6-piperazin-1-ylpyridazine.

$^1$H NMR (400 MHz, CDCl$_3$) δ 7.21 (d, 1H), 6.90 (d, 1H), 3.60 (m, 4H), 3.00 (m, 4H).

Step 2

3-Chloro-6-(4-cyclopropylpiperazin-1-yl)pyridazine

3-Chloro-6-piperazin-1-ylpyridazine (9.93 g, 50 mmol) was suspended in THF (80 mL), and water (18.9 mL), [(1-ethoxycyclopropyl)oxy]trimethylsilan (17.423 g, 100 mmol), acetic acid (8.5 mL, 150 mmol) and sodium cyanoborohydride (4.08 g, 65 mmol) were added. The mixture was heated at 62° C. for 16 h, solvents removed in vacuo and the remainder stirred with DCM (100 mL) and water (75 mL). The pH was adjusted to 10, the organic phase was separated, washed with water and dried over magnesium sulphate. Evaporation in vacuo yielded 3-chloro-6-(4-cyclopropylpiperazin-1-yl)pyridazine as a solid which was recrystallized from acetonitrile to yield the product, 8.18 g, 69%.

$^1$H NMR (400 MHz, CDCl$_3$) δ 7.19 (d, 1H), 6.90 (d, 1H), 3.60 (m, 4H), 2.73 (m, 4H), 1.65 (m, 1H), 0.48 (m, 4H).

Step 3

3-(1,3-Benzodioxol-5-yl)-6-(4-cyclopropylpiperazin-1-yl)pyridazine dihydrochloride 3-Chloro-6-(4-cyclopropylpiperazin-1-yl)pyridazine (8.0 g, 33.5 mmol), acetonitrile (100 mL), 1 M sodium carbonate solution (100.5 mL, 100.5 mmol) and bis(triphenylphosphine)palladium(II) chloride (1.17 g, 1.67 mmol) were mixed and degassed in vacuo under nitrogen. 3,4-Methylenedioxybenzeneboronic acid (8.34 g, 50.3 mmol) was added and the mixture was heated to 80° C. for 16 h. The precipitated product was filtered and washed with acetonitrile and water, and dried in vacuo. The solid was suspended in methanol (500 mL) and 2,2 equivalents of a 4M HCl in dioxane solution was added. The formed solution was filtered, concentrated in vacuo and acetonitrile (100 mL) was added. The suspension was stirred for 1 h, filtered and the solid dried in vacuo to yield 3-(1,3-benzodioxol-5-yl)-6-(4-cyclopropylpiperazin-1-yl) pyridazine as a yellow powder, 11.4 g, 86%.

$^1$H NMR (400 MHz, DMSO-d$_6$) δ 8.37 (d, 1H), 7.95 (d, 1H), 7.65 (d, 1H), 7.62 (dd, 1H), 7.12 (d, 1H), 6.15 (s, 2H), 4.58 (broad d, 2H), 3.30-3.75 (m, 6H) 2.89 (m, 1H), 1.24 (m, 2H), 0.82 (m, 2H).

Microanalysis for C$_{18}$H$_{20}$N$_4$O$_2$, 2×HCl, 1×H$_2$O:
Calc: C, 52.06%; H, 5.82%; N, 13.49%.
Found: C, 51.91%; H, 5.85%; N, 13.57%.

No mutagenic activity has been found for 3-(1,3-benzodioxol-5-yl)-6-(4-cyclopropylpiperazin-1-yl)pyridazine dihydrochloride. Furthermore, in tests with mice, this compound has a reducing effect on the intake of food.

What is claimed is:

1. 3-(1,3-Benzodioxol-5-yl)-6-(4-cyclopropylpiperazin-1-yl)pyridazine or a pharmaceutically acceptable salt, or solvate thereof.

2. The compound of claim 1, where the compound is 3-(1,3-benzodioxol-5-yl)-6-(4-cyclopropylpiperazin-1-yl)pyridazine or solvate thereof.

3. The compound of claim 1, where the compound is a hydrochloride salt of 3-(1,3-benzodioxol-5-yl)-6-(4-cyclopropylpiperazin-1-yl)pyridazine or solvate thereof.

4. The compound of claim 3, where the compound is a 3-(1,3-benzodioxol-5-yl)-6-(4-cyclopropylpiperazin-1-yl) pyridazine dihydrochloride or solvate thereof.

5. A hydrate of a compound, where the compound is 3-(1,3-benzodioxol-5-yl)-6-(4-cyclopropylpiperazin-1-yl)pyridazine or a pharmaceutically acceptable salt thereof.

6. The hydrate of claim 5, where the compound is 3-(1,3-benzodioxol-5-yl)-6-(4-cyclopropylpiperazin-1-yl)pyridazine.

7. The hydrate of claim 5, where the compound is 3-(1,3-benzodioxol-5-yl)-6-(4-cyclopropylpiperazin-1-yl)pyridazine dihydrochloride.

8. The hydrate of claim 6, where the hydrate is a monohydrate.

9. The hydrate of claim 7, where the hydrate is a monohydrate.

10. A pharmaceutical composition comprising a compound of claim 1 and a pharmaceutically acceptable carrier or excipient.

11. A pharmaceutical composition comprising a compound of claim 5 and a pharmaceutically acceptable carrier or excipient.

* * * * *

UNITED STATES PATENT AND TRADEMARK OFFICE
CERTIFICATE OF CORRECTION

| | | |
|---|---|---|
| PATENT NO. | : 8,378,097 B2 | Page 1 of 1 |
| APPLICATION NO. | : 12/302132 | |
| DATED | : February 19, 2013 | |
| INVENTOR(S) | : Hohlweg | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 613 days.

Signed and Sealed this
Second Day of December, 2014

Michelle K. Lee
*Deputy Director of the United States Patent and Trademark Office*